United States Patent

Gallorini

[19]

[11] Patent Number: 5,995,862
[45] Date of Patent: Nov. 30, 1999

[54] SYSTEM FOR MONITORING ULTRAVIOLET RADIATION WITH ASSOCIATED CHECKING OF THE CHARACTERISTICS OF THE SKIN FOR THE ADMINISTRATION OF PROTECTIVE CREAMS

[75] Inventor: Massimo Gallorini, Arezzo, Italy

[73] Assignee: Amon S.R.L., San Marino

[21] Appl. No.: 08/855,001

[22] Filed: May 13, 1997

[30] Foreign Application Priority Data

May 16, 1996 [IT] Italy ................................ FI96A000113

[51] Int. Cl.⁶ ...................................................... A61B 5/05
[52] U.S. Cl. ......................... 600/407; 250/372; 340/600
[58] Field of Search ................................... 600/407, 556, 600/426, 477; 250/372, 372 EM; 340/600; 356/317, 318, 218

[56] References Cited

U.S. PATENT DOCUMENTS

| | | | |
|---|---|---|---|
| 4,704,535 | 11/1987 | Leber et al. | 250/372 |
| 4,962,910 | 10/1990 | Shimizu | 250/372 |
| 4,985,632 | 1/1991 | Bianco et al. | 250/372 |
| 5,008,548 | 4/1991 | Gat | 250/372 |
| 5,036,311 | 7/1991 | Moran et al. | 340/600 |
| 5,305,759 | 4/1994 | Kaneko et al. | 600/476 |
| 5,306,917 | 4/1994 | Black et al. | 250/372 |
| 5,363,854 | 11/1994 | Martens et al. | 600/476 |
| 5,365,068 | 11/1994 | Dickerson | 250/372 |
| 5,439,000 | 8/1995 | Gunderson et al. | 600/473 |

*Primary Examiner*—Brian L. Casler
*Attorney, Agent, or Firm*—McGlew and Tuttle, P.C.

[57] ABSTRACT

The system comprises in combination: a) at least one station (1–13) for detecting the irradiation conditions; b) at least one connection means (19, 21) from said detection station to a user terminal (23); c) at least one detection device (25) for detecting the characteristics of the epidermis of the person who is to be exposed to the ultraviolet radiation; d) correlation means in said user terminal for correlating the irradiation conditions to the characteristics of the epidermis of the person and to the protection factor of any skin-protecting preparations used by the person or to the radiation exposure time, said correlation means indicating the exposure time or the protection factor as a function of the remaining correlated parameters.

15 Claims, 3 Drawing Sheets

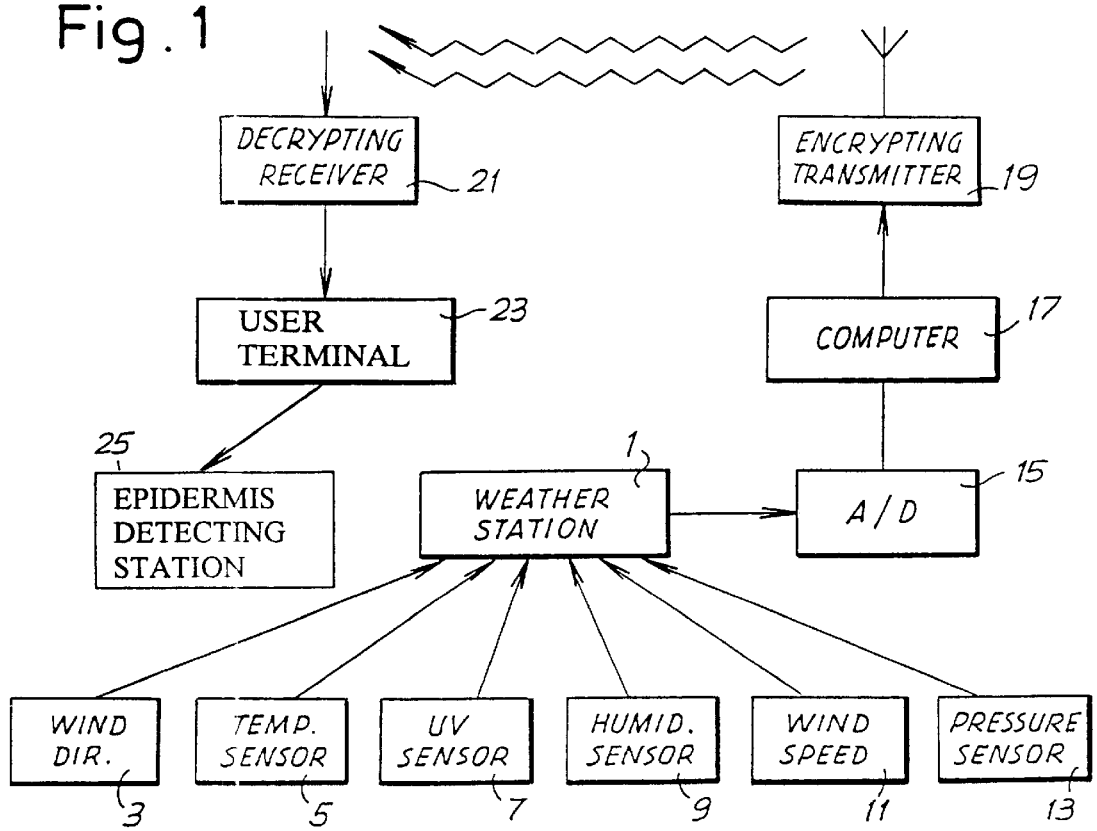
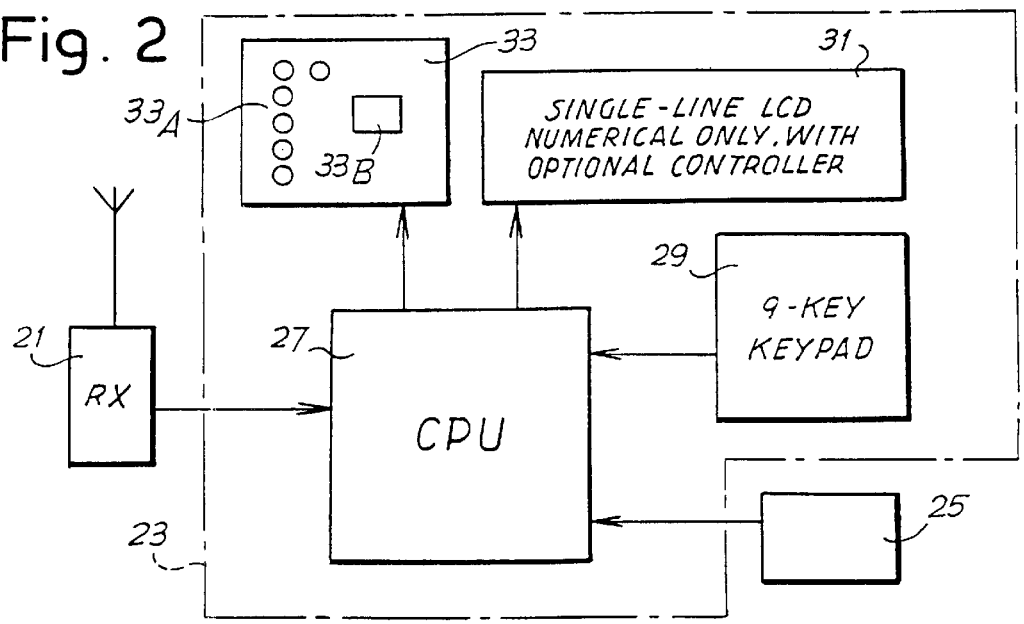

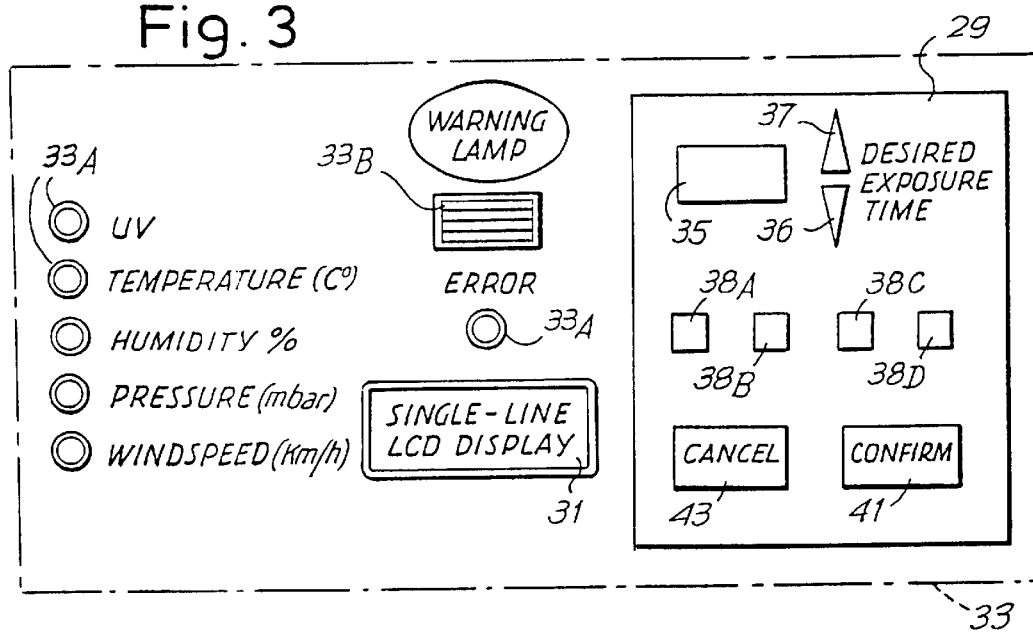
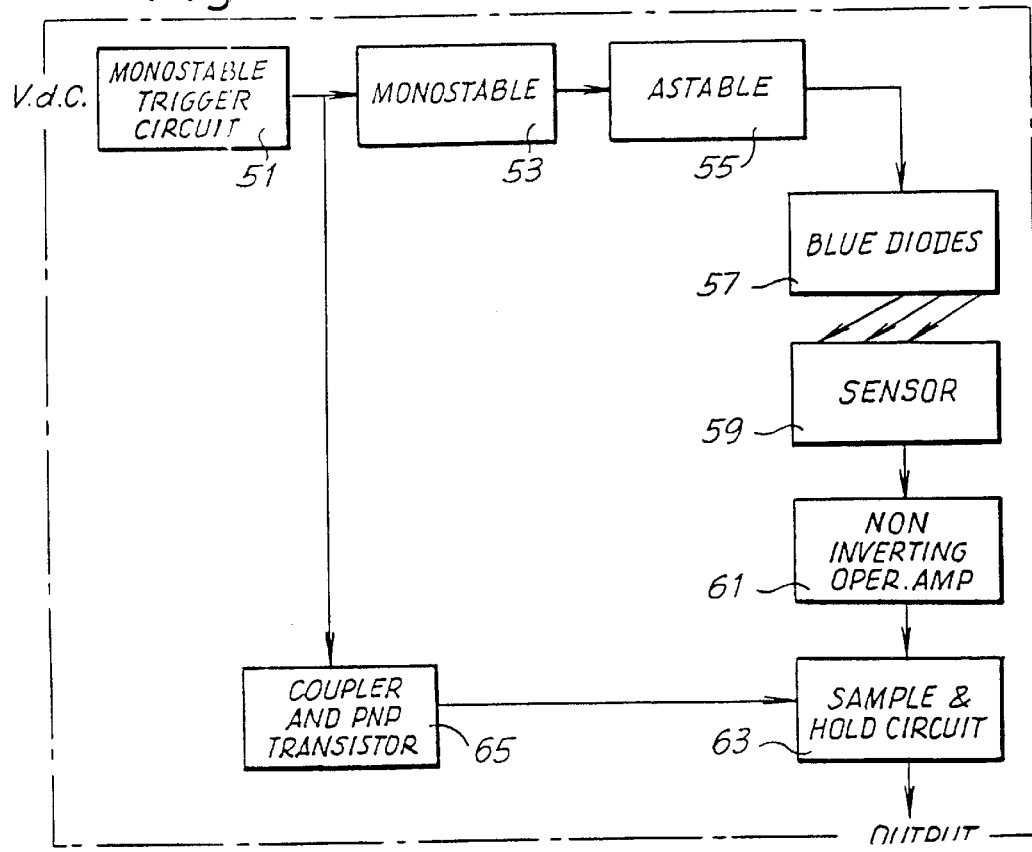

SYSTEM FOR MONITORING ULTRAVIOLET RADIATION WITH ASSOCIATED CHECKING OF THE CHARACTERISTICS OF THE SKIN FOR THE ADMINISTRATION OF PROTECTIVE CREAMS

FIELD AND BACKGROUND OF THE INVENTION

It is known that exposure to solar radiation may have beneficial effects only if suitably controlled so as to prevent erythema, premature ageing or degeneration of a tumorous nature due to over-exposure.

In order to reduce the negative consequences of incorrect or excessive exposure to solar radiation, use is made of protective creams of varying levels which are chosen in a more or less approximate manner depending on the quality of the skin, its degree of tanning and the weather conditions, as well as the exposure time. These precautions are not sufficient in that frequently the evaluation as to the resistance of the epidermis of the person is incorrect, and also because the conditions of solar irradiation may vary greatly depending on the general atmospheric conditions. In general, a correct evaluation of the various parameters which contribute to determining the appropriate protection to be adopted is not possible owing to the part played by subjective factors.

Atmospheric pollution phenomena also make it even more dangerous to submit to ultraviolet radiation for excessively long periods, since no barrier effect against the most harmful ultraviolet radiation is provided by the ozone layer in the upper atmosphere. As is well known, this phenomenon is not noticed by the person who is exposed to the solar radiation except where this has already caused erythema or other more serious damage also affecting other organs and in particular the eyes.

SUMMARY AND OBJECTS OF THE INVENTION

The present invention relates to a system which, with the aid of suitable electronic detection equipment, allows one to check and optimise the conditions of exposure to solar radiation, or more generally to ultraviolet radiation, of various individuals, and which takes account not only of the real irradiation conditions and the atmospheric conditions, but also the characteristics of the epidermis of the individual person (phototype).

The present invention also relates to a device particularly suitable for determining objectively, i.e. with instruments, the condition of the skin so as to evaluate the optimum conditions of exposure to ultraviolet radiation.

In substance, the system according to the invention for monitoring exposure to ultraviolet radiation comprises in combination:

a) at least one station for detecting the irradiation conditions;
b) at least one connection from said detection station to a user terminal;
c) at least one detection device for detecting the characteristics of the epidermis of the person who is to be exposed to the ultraviolet radiation;
d) correlation means in said user terminal for correlating the irradiation conditions to the characteristics of the epidermis of the person and to the protection factor of any skin-protecting preparations used by the person or to the radiation exposure time. The correlation means indicate the exposure time or the protection factor as a function of the remaining correlated parameters.

According to a particularly advantageous embodiment of the system according to the invention, the detection station may comprise, in addition to an ultraviolet radiation sensor for determining the incident energy in this range of wavelengths, additional sensors for detecting one or more parameters relating to the current weather conditions. These sensors may comprise in various combinations one or more of the following sensors: a wind speed sensor, a wind direction sensor, a temperature sensor, a humidity sensor and a barometric pressure sensor.

It is possible, however, for the detection station to be reduced to one or more sensors installed directly on the user terminal, for example to a sensor connected, by a suitable transmission line, to the central processing unit of the user terminal. In this case, the system may also be configured as a portable unit comprising the UV rays sensor, the user terminal and the detection device, all integrated together.

The system will comprise, in general, one or more stations for detecting the ultraviolet radiation depending on the size of the system itself. These stations form the centers of a network for the distribution of information (via cable or via radio or the like) to a plurality of user terminals so as to transmit to the terminals the information relating to the irradiation conditions and any additional information relating to the weather conditions.

The information relating to the phototype may be entered into the user terminal via a keyboard in an empirical manner, but in order to obtain a more accurate and objective check, based on measurements using instruments rather than on a subjective perception of how tanned and/or resistant the epidermis is, and hence in order to determine with greater precision the conditions to which the person may be exposed to the solar radiation, the system envisages that the means for detecting the characteristics of the epidermis have an emitter which emits radiation close to or within the ultraviolet range, and a detector which detects the radiation emitted by said emitter and reflected by the epidermis. Such an instrument can output information which is objective, i.e. determined with instruments, regarding the characteristics of the epidermis.

With the correlation means present in the user terminal it is possible to determine, on the basis of the information received, the optimum conditions for each individual person under which the latter may be exposed to solar radiation.

The user terminal may comprise a programmable central processing unit which receives the various types of information from the station for detecting the irradiation and any other parameters relating to the weather conditions and the information relating to the individual phototype. The central processing unit may be programmed in such a way as to determine, on the basis of the information received, the optimum irradiation conditions in terms of time or protective factor to be applied to the epidermis. According to an improved embodiment of the invention, the central processing unit may also provide an alarm signal when one or more of the conditions detected by the detection station exceeds an alarm threshold. This is a case which occurs for example when the ultraviolet radiation reaching the sensor of the detection station is greater than a safety threshold, beyond which, even in the presence of a high protective factor, the epidermis subjected to irradiation may undergo damage, possibly of a serious nature, and/or the use of sun-glasses is required.

Further advantages characteristic features of the system according to the invention are indicated in the accompanying claims.

The invention also relates to a device for determining the characteristics of the epidermis of a person, comprising in combination: an emitter which emits electromagnetic radiation towards the epidermis; and a receiver which receives the electromagnetic radiation emitted by said emitter and reflected by the epidermis, said receiver generating a signal correlated to the intensity of the radiation received. The device may be used within the context of the system described above, or else separately or in combination with other equipment, for example in combination with a UV radiation detector which, carried by the user, may alert the latter when the exposure exceeds the maximum value compatible with his/her phototype and with the protection factor of the cream used.

The device may be equipped with a system for generating UV rays, for example a UV lamp, which may also be used for sterilizing the device so as to ensure optimum conditions of hygienic use, even in the case of use by a plurality of users.

The invention will be understood more fully with reference to the description and the accompanying drawing, which shows a practical non-limiting example of an embodiment of the invention. In the drawing:

BRIEF DESCRIPTION OF THE DRAWINGS

FIG. 1 shows a block diagram of a system according to the invention in a particularly simple configuration;

FIG. 2 shows a block diagram of the user terminal;

FIG. 3 shows a possible embodiment of the control panel of the user terminal;

FIG. 4 shows a block diagram of the device for detecting the characteristics of the epidermis of the person who is to be exposed to ultraviolet radiation.

DETAILED DESCRIPTION OF THE PREFERRED EMBODIMENT

Figure 5:
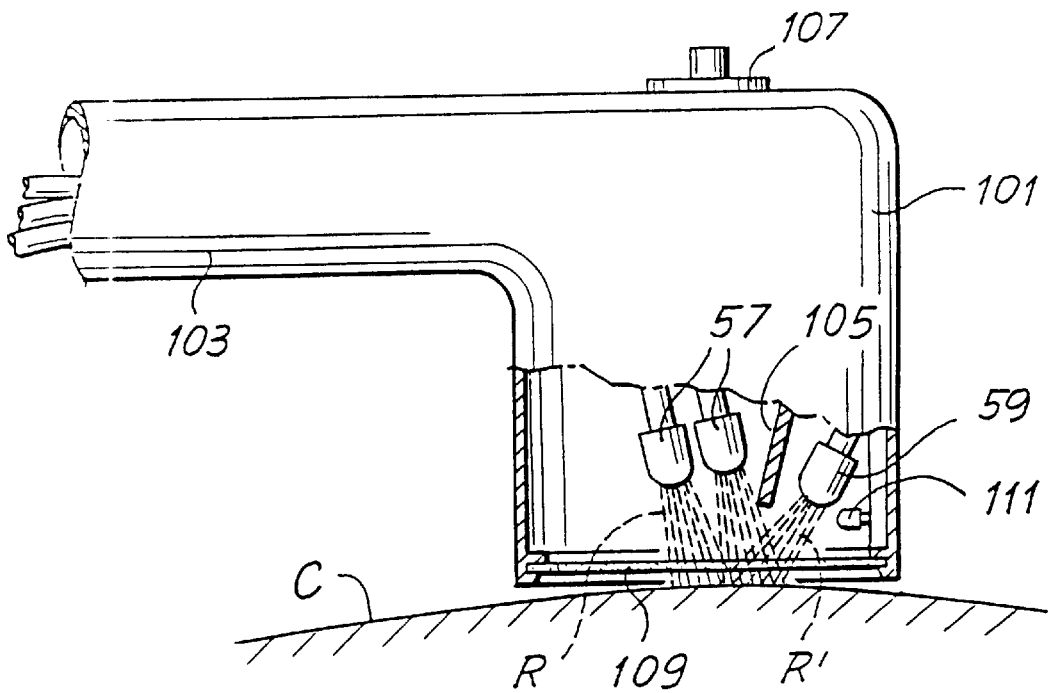
FIG. 5 shows a constructional diagram for said detection device.

With initial reference to FIG. 1, the system in the minimum configuration illustrated therein comprises a detection station 1 which receives information from a plurality of sensors 3, 5, 7, 9, 11 and 13. These sensors may consist of an ultraviolet radiation sensor (sensor 7) and sensors for weather parameters such as the wind direction (sensor 3), the temperature (sensor 5), the atmospheric humidity (9), the wind speed (sensor 11) and the atmospheric pressure (sensor 13). The data from the sensors 3 to 13 is converted by means of an analog-digital converter 15 and sent to a computer 17 which, for example by means of a radio transmitter 19, sends the information (if necessary suitably encrypted) to a receiver 21 associated with a user terminal 23. The receiver 21 may decrypt the data received.

25 denotes in general on epidermis detection device for detecting the characteristics of the epidermis of the individual users of the system. A detailed description of the structure of this detection device, which per se forms a subject of the present invention, will be provided below.

In the block diagram shown in FIG. 1 a single detection station 1 and a single user terminal 23 with the associated receiver 21 are shown. It is obvious, however, that the system may be expanded in whatever way may be considered most appropriate and in accordance with the requirements of the users, by adding more detection stations 1 and a plurality of user terminals 23 equipped with associated receivers 21. The data detected by the detection station 1 is encoded and transmitted via the transmitter 19 to one or more receivers 21 associated with corresponding terminals 23, a certain number of times per day, at a rate which can be programed in accordance with, e.g., the variability of the atmospheric conditions in the specific area in which the system is installed.

As regards the detection station 1, the ultraviolet sensor 7 is of particular importance. The latter is chosen for example with a spectral response ranging between 260 and 310 nanometers and with working temperatures ranging between −10 and +80° C. A possible sensor for this application is for example the C5842 series semiconductor UV sensor produced by Hamatsu Phbtonics K. K. Japan. This sensor has a spectral response range centred on the wavelength of UVB radiation (280–320 nanometers) which represents the most dangerous radiation since it is not absorbed by the atmosphere.

The data detected by the individual sensors 3 to 13 associated with the detection station 1 is converted into numerical data by the analog-digital converter 15 which in polling mode, without speed problems, interrogates the various sensors at suitable time intervals. The information in digital form is conveyed from one or more detection stations 1 to the computer 17 for transmission.

FIG. 2 shows a block diagram of the assembly consisting of the receiver 21 and the user terminal 23. The terminal 23 comprises a central processing unit 27 which receives the data from the receiver 21 as well as from the device 25 for detecting the characteristics of the epidermis of the person who is exposed to the ultraviolet radiation. A key-pad 29, shown in detail in FIG. 3, allows additional data to be entered in the central processing unit 27 for determining the exposure time and/or the protection factor to be used. The central processing unit 27 is also connected to a display 31 for presenting the data which will be described below and to an assembly 33 comprising a plurality of luminous indicator lamps 33A and an acoustic signalling device 33B for signalling alarm situations.

As can be seen in FIG. 3, on the key-pad 29 there are nine push-buttons with the following functions: a first push-button 35 starts the procedure for reading, by means of the detection device 25, the characteristics of the user's skin; a pair of push-buttons 36, 37 are for entering the exposure time in the manner described below; a series of four push-buttons 38A, 38B, 38C and 38D are for entering the protection factor of the protective cream used; a push-button 41 is for confirming the data entered and a push-button 43 is used to cancel the data entered in the event of errors.

FIG. 4 shows a functional block diagram of the detection device 25. It has a circuit 51 for triggering a monostable vibrator 53 connected to an astable vibrator 55 which controls a pair of blue diodes 57 in series. Connected to the latter is a detector, consisting for example of a phototransistor schematically indicated at 59, the output signal of which is sent to a non-inverting operational amplifier 61, the output of which is connected to a sample-and-hold circuit 63. The output of the circuit 63 is sent to the central processing unit 27. 65 denotes generally a coupler and a PNP-type transistor.

The detecting device 25 is based on the photo-reflective capacity of the skin and simulates the UV component of the solar rays which strike the epidermis. This result is possible owing to the use of the blue diode 57 which has an emission which reaches the ultraviolet range. During the measurement, the equipment is placed on the skin in the desired area, so that the light emitted by the diode 57 is reflected by the skin and the reflected signal is captured by the sensor 59. The resistance of the sensor varies on the basis of the light intensity reflected by the epidermis and the detected variation in resistance is transmitted to a graphic display device (not shown) as well as to the central processing unit 27 to which the device 25 is connected.

FIG. 5 shows schematically the arrangement of the diodes 57 and the phototransistor 59. They are housed inside a rigid container 101 which can be easily gripped by means of a handle 103 and are separated from each other by an obscuring baffle 105, which prevents direct irradiation of the phototransistor 59 by the diodes 57. On the top end of the device is a push-button 107 which, once pressed, sends a pulse to the monostable vibrator 53, by means of the trigger circuit 51, so as to activate the astable vibrator 55 which supplies the diode 57 with a train of pulses which cause the latter to flash at a frequency which can be read by the sensor 59. The voltage output by the sensor 59, amplified by the operational amplifier 61, is retained in the sample-and-hold circuit 63 where the data is stored until read subsequently.

At the front the container 101 is closed by a glass window 109 which is transparent to the radiation of the diodes 57. During use the device is placed with the glass window 109 on a point of the body C of the user and, via the push-button 107, the process of detecting the characteristics of the epidermis in the test area is started. The radiation R emitted by the diodes 57 passes through the glass window 109, reaches the user's skin and is partially reflected by the latter. The reflected radiation R' is received by the phototransistor 59.

In order to increase the sensitivity of the device, in view of the low power of emission of the blue diodes 57 currently available, the device is provided with an auxiliary polarizing diode 111, for example a red emitting diode, which brings the phototransistor 59 into the useful working zone. This diode is powered at 12 V d.c. with a resistance of 47 kiloohms.

The emitting diodes 57 are arranged in series and supplied with pulses at a frequency of 5 kHz at 12 V with a duty cycle of about 50%. The time period of the monostable 53 which enables emission of the blue diodes is about 3 seconds.

Below a description is provided of the procedure for calculating the times for exposure to the ultraviolet rays, depending on the phototype and the protective factor of any cream used.

The parameters which are considered in the calculation algorithm are as follows:
1. Phototype: this is a parameter which defines the greater or lesser resistance of the skin of the individual person to ultraviolet radiation and its capacity for tanning. The phototype is determined by the device 25 from the value read by the sensor 59 which is translated into a numerical parameter on a suitable scale, for example four values divided up as follows: phototype 1, delicate skin extremely prone to burns; phototype 2, fairly delicate skin prone to burns; phototype 3, normal skin which may burn following prolonged exposure; phototype 4, resistant skin which is not prone to burns and tans easily or is already naturally dark;
2. Sun protection factor: represents the protection factor of the skin-protecting cream used. It is possible to envisage using a scale of five values from zero to four corresponding to no protection, minimum protection, low protection, average protection and high protection;
3. Intensity of the ultraviolet radiation: according to the now accepted international standard for quantification of ultraviolet radiation, the intensity of the radiation is divided up into five levels corresponding to minimum, low, average, high and very high.

The exposure time which ensures that burns are avoided is determined as a function which is directly proportional to the phototype and to the protection factor and inversely proportional to the intensity of irradiation by the ultraviolet rays, in accordance with the formula:

$$T = k*(F*SPF)/UV$$

where
- k is a proportionality constant,
- T is the exposure time,
- UV is the intensity of the ultraviolet radiation represented by a number corresponding to one of the five levels mentioned above,
- F is the phototype and corresponds to a number from 1 to 4 as indicated above,
- SPF is the sun protection factor and varies from 1 to 4.

The value of the UV parameter is supplied by the detection station 1, via the receiver 21, to the central processing unit 27, while the parameter F is supplied by the device 25 via the sensor 59. The SPF factor is entered via the key-pad 29 using one of the keys 38A, 38B, 38C, 38D.

For a more accurate measurement, the term k may in turn be a variable dependent on, for example, the weather parameters other than the UV radiation, for example the humidity or the wind. The reason for this is that these weather parameters influence sweating and hence removal of the protective cream from the user's skin. The greater the sweating (caused by unfavourable weather conditions), the shorter is the exposure time without risk.

Having defined the parameters for calculation of the exposure time, the operating cycle of the user terminal 23 will now be described.

When the terminal is not used for determining the optimum conditions for exposure to ultraviolet radiation and is, therefore, in standby mode, the data detected by the detection station 1 and transmitted to the terminal 23 may appear in sequence on the display 31, for example in the sequence: intensity of ultraviolet radiation, temperature, humidity, barometric pressure, wind speed. These values are updated at time intervals which can be predetermined and are stored in the internal registers of the user terminal 23.

When one of the weather parameters detected exceeds an alarm condition, the central processing unit 27 emits an alarm signal via one of the LEDs 33A and/or via the acoustic warning device 33B. The alarm conditions may consist of an excessive ultraviolet radiation level, a sharp drop in atmospheric pressure or a wind speed greater than a predetermined threshold. The conditions listed may also be concurrent and, when one of them occurs, the corresponding LED will light up and in addition a flashing luminous indicator lamp and an acoustic signal via the warning device 33B may be provided. The alarm signal may continue for a programmable period of time, for example one minute, after which the luminous and acoustic warning devices will switch off and be reactivated after a time interval, for example 15 minutes, should the alarm conditions persist.

When a user wishes to determine, via the user terminal 23, the optimum conditions for exposure to the ultraviolet radiation, and if the aforementioned alarm conditions do not occur, he/she is able to activate the terminal by pressing any key on the key-pad 29, causing the system to exit from the standby condition described above and thus placing the terminal itself in the condition for calculating the solar exposure parameters. At this point the push-button 35 is pressed in order to activate the calculation sequence. By means of the device 25, connected via a cable to the user terminal 23, the user is able to carry out a sequence of, e.g., three measurements on different areas of his/her skin. The three measurements provide three values of the phototype F which are shown in turn on the display 31. The central processing unit 27 will calculate an average value of these three values.

At this point, two possibilities may be envisioned: the user may determine the optimum exposure time, the skin protection factor used already being known; or else the user may enter the desired exposure time and find out what skin-protection factor to use so that, in the current irradiation conditions and for his/her phototype, the risk of burning is avoided.

In the first case, the user will provide the central processing unit 27, by means of one of the keys 38A–38D, with a value corresponding to the SPF protection factor. The data entered will appear on the display 31 and may be confirmed with the key 41 or cancelled using the key 43. Once the data relating to the protection factor has been confirmed, a numerical factor will appear on the display corresponding to the time expressed in hours or in fractions, which guarantees, with respect to the present ultraviolet radiation, the phototype and the skin protection factor entered, tanning without the risk of burning.

The central processing unit 27 may be programmed so that, if the values entered result in a time greater than two hours, this information will be shown flashing on the display 31 and may, if necessary, be accompanied by an acoustic signal via the warning device 33B, so as to indicate to the user that, in view of the considerable exposure time and the possibility that the skin protection cream may be removed by bathing, and in particular in view of the fact that the level of ultraviolet irradiation may vary considerably during the time interval calculated, it is recommended to repeat the measurement and if necessary also the application of the skin protection cream.

In the second case, a user who does not have a suitable skin protection cream will press any of the keys 38A–38D as in the case above. At this point he/she may enter by means of the dual push-button 36, 37 the desired exposure time which can be read on the display 31. When the desired exposure time appears on the display, the confirm key 41 will be pressed. Once the data has been confirmed, the display will indicate the protection factor to be adopted.

Here again, if the time entered exceeds two hours, a flashing signal will be provided by the system, advising repetition of the measurement and/or application of the skin protection cream.

The central processing unit 27 is programmed so that the operations described above must be carried out within a predefined time interval, for example three minutes, after which the unit will set itself in the condition for receiving the data relating to a new person so as to carry out a new calculation.

It is understood that the drawing shows only an example provided purely by way of a practical demonstration of the invention, said invention being able to be varied as regards its forms and arrangements without, however, departing from the scope of the idea underlying the invention.

I claim:

1. A system for monitoring exposure to ultraviolet radiation, comprising in combination:
   a) a user terminal and at least one detection station for detecting irradiation conditions;
   b) a connection from said detection station to said user terminal;
   c) at least one detection device for detecting characteristics of an epidermis of a person who is to be exposed to the ultraviolet radiation;
   d) correlation means in said user terminal for correlating the irradiation conditions to the characteristics of the epidermis of the person and to one of a protection factor of any skin-protecting preparations used by the person and to a radiation exposure time, said correlation means indicating the exposure time or the protection factor as a function of remaining correlated parameters.

2. The system as claimed in claim 1, wherein:
   said detection station comprises an ultraviolet radiation sensor and at least one sensor for sensing weather conditions, selected from the group comprising: a wind speed sensor, a temperature sensor, a humidity sensor, a wind direction sensor and a barometric pressure sensor.

3. The system as claimed in claim 1, in which said detection station is connected via radio to at least one said user terminals so as to transmit to said terminals detected information relating to the irradiation conditions and to any additional weather data.

4. The system as claimed in claim 1, in which said detection device comprises: an emitter which emits radiation at a wavelength which reaches the UV range; and a detector which detects the radiation emitted by said emitter and reflected by the skin of the person.

5. The system as claimed in claim 1, in which said user terminal comprises a central processing unit which receives the information from said detection station and data detected by said detection device relating to the characteristics of the epidermis of the person.

6. The system as claimed in claim 5, in which said central processing unit is connected to keyboard entry means for entering additional parameters which can be correlated to the information from the detection station and from the device for detecting the characteristics of the epidermis.

7. The system as claimed in claim 5, in which said central processing unit is connected to display means.

8. The system as claimed in claim 5, in which said central processing unit is connected to alarm means and is programmed so as to emit an alarm signal when one or more of the parameters relating to the conditions detected by the said detection station exceed a maxium safety threshold.

9. The system in accordance with claim 1, wherein:
   said detection device includes an emitterwhich emits electromagnetic radiation towards the epidermis and includes a receiver which receives the electromagnetic radiation emitted by said emitter and reflected by the epidermis, said receiver generating a signal correlated to an intensity of the radiation received.

10. The system as claimed in claim 9, in which said emitter comprises at least one source which emits within the UV radiation range.

11. The system as claimed in claim 9, in which said receiver comprises a phototransistor.

12. The system as claimed in claim 11, further comprising:
   an emitter diode for polarization of the phototransistor.

13. The system as claimed in claim 10, wherein:
   said source is an emitting diode.

14. The system as claimed in claim 9, wherein:
   said emitter includes a UV radiation source of a type used for sterilization.

15. A system for monitoring exposure to ultraviolet radiation, the system comprising:
   a detection station for detecting an irradiation condition;
   a user terminal in connection with said detection station, said user terminal including a detection device for detecting a characteristic of an epidermis of a person who is to be exposed to the ultraviolet radiation, said user terminal also including correlation means for correlating the irradiation condition to the characteristic of the epidermis of the person and to one of a protection factor of any skin-protecting preparations used by the person and to a radiation exposure time, said correlation means indicating one of an exposure time or protection factor as a function of remaining said characteristics and condition.

* * * * *